US011499916B2

(12) United States Patent
Purves et al.

(10) Patent No.: US 11,499,916 B2
(45) Date of Patent: Nov. 15, 2022

(54) SPECTROSCOPY SYSTEM AND METHOD OF PERFORMING SPECTROSCOPY

(71) Applicant: Picomole Inc., Moncton (CA)

(72) Inventors: Christopher Quentin Purves, Moncton (CA); Denis Dufour, Montreal (CA)

(73) Assignee: PICOMOLE INC., Halifax (CA)

( * ) Notice: Subject to any disclaimer, the term of this patent is extended or adjusted under 35 U.S.C. 154(b) by 154 days.

(21) Appl. No.: 16/599,943

(22) Filed: Oct. 11, 2019

(65) Prior Publication Data

US 2020/0319028 A1     Oct. 8, 2020

Related U.S. Application Data

(60) Provisional application No. 62/828,750, filed on Apr. 3, 2019.

(51) Int. Cl.
| | |
|---|---|
| *G01J 3/26* | (2006.01) |
| *G01N 21/39* | (2006.01) |
| *G01N 33/497* | (2006.01) |
| *G01N 1/40* | (2006.01) |
| *G01J 3/42* | (2006.01) |

(Continued)

(52) U.S. Cl.
CPC .......... *G01N 21/39* (2013.01); *G01J 3/0205* (2013.01); *G01J 3/10* (2013.01); *G01J 3/42* (2013.01); *G01N 1/40* (2013.01); *G01N 21/31* (2013.01); *G01N 21/3504* (2013.01); *G01N 21/552* (2013.01); *G01N 33/497* (2013.01); *G01J 2003/423* (2013.01); *G01N 2021/391* (2013.01); *G01N 2021/398* (2013.01); *G01N 2021/7789* (2013.01); *G01N 2033/4975* (2013.01); *G06N 20/00* (2019.01)

(58) Field of Classification Search
CPC .... G01N 21/39; G01N 21/31; G01N 21/3504; G01N 21/552; G01N 33/497; G01N 1/40; G01N 2021/7789; G01N 2021/391; G01N 2033/4975; G01N 2021/398; G01J 3/10; G01J 3/0205; G01J 3/42; G01J 2003/423; G06N 20/00

See application file for complete search history.

(56) References Cited

U.S. PATENT DOCUMENTS

| | | |
|---|---|---|
| 3,431,514 A | 3/1969 | Harris |
| 3,453,557 A | 7/1969 | Tobias |

(Continued)

FOREIGN PATENT DOCUMENTS

| | | |
|---|---|---|
| CA | 2792032 A1 | 9/2011 |
| CA | 2892870 A1 | 11/2015 |

(Continued)

OTHER PUBLICATIONS

Final Office Action for U.S. Appl. No. 16/509,207 dated Oct. 7, 2020.

(Continued)

*Primary Examiner* — Abdullahi Nur

(57) ABSTRACT

A spectroscopy system is disclosed, and includes a resonant cavity, a first conduit configured to couple at a first end thereof to a gas source, and at a second end thereof to a first end of a sorbent tube containing a sample for analysis, and a second conduit configured to couple at a first end thereof to a second end of the sorbent tube, and at a second end thereof to the resonant cavity.

25 Claims, 7 Drawing Sheets

(51) Int. Cl.
  *G01N 21/3504*  (2014.01)
  *G01N 21/552*  (2014.01)
  *G01J 3/02*  (2006.01)
  *G01N 21/31*  (2006.01)
  *G01J 3/10*  (2006.01)
  G06N 20/00  (2019.01)
  G01N 21/77  (2006.01)

(56) References Cited

U.S. PATENT DOCUMENTS

| | | | |
|---|---|---|---|
| 3,517,330 | A | 6/1970 | Doyle |
| 3,534,289 | A | 10/1970 | Clark |
| 3,596,201 | A | 7/1971 | Chester |
| 3,628,173 | A | 12/1971 | Danielmeyer |
| 3,733,129 | A | 5/1973 | Bridges |
| 4,197,513 | A | 4/1980 | Bell |
| 4,410,271 | A | 10/1983 | Matthews |
| 4,468,773 | A | 8/1984 | Seaton |
| 4,475,199 | A | 10/1984 | Sanders |
| 4,648,714 | A | 3/1987 | Benner et al. |
| 4,672,618 | A | 6/1987 | Wijntjes |
| 4,779,279 | A | 10/1988 | Brown |
| 4,784,486 | A | 11/1988 | Van Wagenen et al. |
| 4,964,132 | A | 10/1990 | Fischer |
| 5,014,278 | A | 5/1991 | Deki |
| 5,029,174 | A | 7/1991 | Anderson |
| 5,054,027 | A | 10/1991 | Goodberlet |
| 5,091,912 | A | 2/1992 | Bretenaker |
| 5,135,304 | A | 8/1992 | Miles et al. |
| 5,386,833 | A | 2/1995 | Uhen |
| 5,465,728 | A | 11/1995 | Phillips |
| 5,528,040 | A | 6/1996 | Lehmann |
| 5,573,005 | A | 11/1996 | Ueda et al. |
| 5,636,035 | A | 6/1997 | Whittaker |
| 5,646,952 | A | 7/1997 | Whittley |
| 5,720,650 | A * | 2/1998 | Mauze ............... G01N 21/15 451/39 |
| 5,815,277 | A | 9/1998 | Zare et al. |
| 5,903,358 | A | 5/1999 | Zare et al. |
| 5,912,740 | A | 6/1999 | Zare et al. |
| 6,076,392 | A | 6/2000 | Drzewiecki |
| 6,084,682 | A | 7/2000 | Zare et al. |
| 6,233,052 | B1 | 5/2001 | Zare et al. |
| 6,324,191 | B1 | 11/2001 | Horvath |
| 6,363,772 | B1 | 4/2002 | Berry |
| 6,466,322 | B1 | 10/2002 | Paldus et al. |
| 6,479,019 | B1 | 11/2002 | Goldstein et al. |
| 6,488,639 | B1 | 12/2002 | Ribault |
| 6,504,145 | B1 | 1/2003 | Romanini et al. |
| 6,540,691 | B1 | 4/2003 | Phillips |
| 6,541,271 | B1 | 4/2003 | McFarland |
| 6,563,583 | B2 | 5/2003 | Ortyn et al. |
| 6,582,376 | B2 | 6/2003 | Baghdassarian |
| 6,633,596 | B1 | 10/2003 | Wulfmeyer |
| 6,658,034 | B2 | 12/2003 | Gamache et al. |
| 6,726,637 | B2 | 4/2004 | Phillips |
| 6,727,492 | B1 | 4/2004 | Ye et al. |
| 6,865,198 | B2 | 3/2005 | Taubman |
| 6,952,945 | B2 | 10/2005 | O'Brien |
| 6,958,446 | B2 | 10/2005 | Humpston |
| 7,004,909 | B1 | 2/2006 | Patel et al. |
| 7,012,696 | B2 | 3/2006 | Orr et al. |
| 7,101,340 | B1 | 9/2006 | Braun |
| 7,106,763 | B2 | 9/2006 | Tan et al. |
| 7,235,054 | B2 | 6/2007 | Eckerbom |
| 7,352,463 | B2 | 4/2008 | Bounaix |
| 7,391,517 | B2 | 6/2008 | Trebbia et al. |
| 7,450,240 | B2 | 11/2008 | Morville et al. |
| 7,538,881 | B2 | 5/2009 | Ye et al. |
| 7,541,586 | B2 | 6/2009 | Miller |
| 7,555,024 | B2 | 6/2009 | Ishaaya et al. |
| 7,569,823 | B2 | 8/2009 | Miller |
| 7,606,274 | B2 | 10/2009 | Mirov et al. |
| 7,612,885 | B2 | 11/2009 | Cole et al. |
| 7,613,216 | B2 | 11/2009 | Nakagawa |
| 7,616,123 | B2 | 11/2009 | Ridder et al. |
| 7,646,485 | B2 | 1/2010 | Tan |
| 7,679,750 | B2 | 3/2010 | Li et al. |
| 7,902,534 | B2 | 3/2011 | Cole et al. |
| 8,018,981 | B2 | 9/2011 | Eckles et al. |
| 8,109,128 | B2 | 2/2012 | Kalkman et al. |
| 8,288,727 | B2 | 10/2012 | Cormier et al. |
| 8,322,190 | B2 | 12/2012 | Kalkman et al. |
| 8,437,000 | B2 | 5/2013 | Cole et al. |
| 8,488,639 | B1 | 7/2013 | Diels et al. |
| 8,564,785 | B2 | 11/2013 | Newbury et al. |
| 8,659,758 | B2 | 2/2014 | Koulikov et al. |
| 8,659,759 | B2 | 2/2014 | Koulikov et al. |
| 8,665,442 | B2 | 3/2014 | Koulikov et al. |
| 8,885,167 | B2 | 11/2014 | Koulikov et al. |
| 8,958,446 | B2 | 2/2015 | Hirose |
| 8,982,352 | B1 | 3/2015 | Hoffnagle et al. |
| 9,014,221 | B2 | 4/2015 | Kub et al. |
| 9,029,819 | B2 | 5/2015 | Zhu et al. |
| 9,044,565 | B2 | 6/2015 | Colman et al. |
| 9,086,421 | B1 | 7/2015 | Miller |
| 9,097,583 | B2 | 8/2015 | Gupta et al. |
| 9,194,742 | B2 | 11/2015 | Kachanov et al. |
| 9,207,121 | B2 | 12/2015 | Adler |
| 9,212,990 | B1 | 12/2015 | Muraviev |
| 9,568,465 | B2 | 2/2017 | Rihani et al. |
| 9,625,702 | B2 | 4/2017 | Hodges et al. |
| 9,643,186 | B1 | 5/2017 | Ahmad et al. |
| 9,653,877 | B1 | 5/2017 | Arissian et al. |
| 9,671,332 | B2 | 6/2017 | Christensen |
| 9,755,399 | B2 | 9/2017 | Tulip |
| 9,768,347 | B2 | 9/2017 | Teo |
| 9,778,110 | B1 | 10/2017 | Rella et al. |
| 9,918,661 | B2 | 3/2018 | Cormier et al. |
| 10,034,621 | B2 | 7/2018 | Wondka et al. |
| 10,101,268 | B2 | 10/2018 | Apolonskiy et al. |
| 10,130,284 | B2 | 11/2018 | Johnson |
| 10,139,392 | B2 | 11/2018 | Kaariainen et al. |
| 10,141,713 | B2 | 11/2018 | Kim et al. |
| 10,168,275 | B2 | 1/2019 | Orcutt |
| 10,194,833 | B2 | 2/2019 | Cormier |
| 10,234,381 | B2 | 3/2019 | Koulikov |
| 10,286,176 | B2 | 5/2019 | Zapol et al. |
| 10,330,592 | B2 | 6/2019 | Koulikov |
| 10,401,281 | B2 | 9/2019 | Koulikov |
| 10,499,819 | B2 | 12/2019 | Wondka et al. |
| 10,527,492 | B2 | 1/2020 | Bouzid |
| 10,620,048 | B2 | 4/2020 | Allison |
| 2003/0109055 | A1 | 6/2003 | Lehmann |
| 2003/0109794 | A1 | 6/2003 | Phillips |
| 2003/0189711 | A1 | 10/2003 | Orr et al. |
| 2004/0022281 | A1 | 2/2004 | Steffens et al. |
| 2004/0074303 | A1 | 4/2004 | Matsiev |
| 2004/0137637 | A1 | 7/2004 | Wang et al. |
| 2004/0142484 | A1 | 7/2004 | Berlin et al. |
| 2004/0162500 | A1 | 8/2004 | Kline |
| 2004/0190563 | A1 | 9/2004 | Gendron |
| 2005/0122520 | A1 | 6/2005 | Yan |
| 2005/0134836 | A1 | 6/2005 | Paldus et al. |
| 2005/0177056 | A1 | 8/2005 | Giron et al. |
| 2005/0177057 | A1 | 8/2005 | Friedman et al. |
| 2005/0201428 | A1 | 9/2005 | Cotteverte |
| 2005/0213617 | A1 | 9/2005 | Gendron |
| 2005/0254535 | A1 | 11/2005 | Loewen et al. |
| 2006/0200037 | A1 | 9/2006 | Falasco |
| 2006/0233205 | A1 | 10/2006 | Farmiga |
| 2007/0008995 | A1 | 1/2007 | Oozeki |
| 2007/0062255 | A1 | 3/2007 | Talton |
| 2007/0091941 | A1 | 4/2007 | Mori |
| 2007/0133001 | A1 | 6/2007 | Cox et al. |
| 2007/0195434 | A1 | 8/2007 | Koulikov |
| 2007/0268941 | A1 | 11/2007 | Kim et al. |
| 2008/0091085 | A1 | 4/2008 | Urushihata et al. |
| 2008/0139021 | A1 | 6/2008 | Suzuki et al. |
| 2008/0170597 | A1 | 7/2008 | van der Veer |
| 2009/0201957 | A1 | 8/2009 | Brotherton-Ratcliffe |
| 2009/0232172 | A1 | 9/2009 | Masuda |
| 2009/0306527 | A1 | 12/2009 | Kubo et al. |

(56) References Cited

U.S. PATENT DOCUMENTS

| | | |
|---|---|---|
| 2010/0002234 A1 | 1/2010 | Cormier et al. |
| 2010/0074089 A1 | 3/2010 | Smith |
| 2010/0135342 A1 | 6/2010 | Livas |
| 2010/0277737 A1* | 11/2010 | Tuchman .............. G01N 21/39 356/437 |
| 2011/0072887 A1 | 3/2011 | Oki |
| 2011/0192213 A1 | 8/2011 | Zimmerman |
| 2011/0216311 A1 | 9/2011 | Kachanov et al. |
| 2011/0269632 A1 | 11/2011 | Haick |
| 2011/0295140 A1 | 12/2011 | Zaidi et al. |
| 2012/0103062 A1 | 5/2012 | Hsiao |
| 2012/0143805 A1 | 6/2012 | Gold et al. |
| 2012/0183949 A1 | 7/2012 | Hyde et al. |
| 2012/0250706 A1 | 10/2012 | Stiens |
| 2012/0257218 A1 | 10/2012 | Pinel |
| 2012/0266883 A1 | 10/2012 | Taylor et al. |
| 2012/0294876 A1 | 11/2012 | Zimmerman |
| 2012/0309048 A1 | 12/2012 | Ratcliffe et al. |
| 2013/0017618 A1 | 1/2013 | Hargrove |
| 2013/0144561 A1 | 6/2013 | Harb et al. |
| 2013/0228688 A1 | 9/2013 | Plusquellie et al. |
| 2013/0303929 A1 | 11/2013 | Martino et al. |
| 2014/0125993 A1 | 5/2014 | Kachanov et al. |
| 2014/0276100 A1 | 9/2014 | Satterfield et al. |
| 2014/0293283 A1 | 10/2014 | Farooq et al. |
| 2014/0320856 A1 | 10/2014 | McKeever et al. |
| 2015/0032019 A1 | 1/2015 | Acker et al. |
| 2015/0077747 A1 | 3/2015 | Smith et al. |
| 2015/0138558 A1 | 5/2015 | Kachanov et al. |
| 2015/0335206 A1 | 11/2015 | Stafford |
| 2015/0335267 A1 | 11/2015 | Cormier et al. |
| 2016/0069795 A1 | 3/2016 | Koulikov |
| 2016/0174875 A1 | 6/2016 | Forster et al. |
| 2016/0285236 A1 | 9/2016 | Yvind |
| 2016/0313233 A1 | 10/2016 | Zangmeister et al. |
| 2017/0074857 A1 | 3/2017 | Dennis et al. |
| 2017/0373462 A1 | 12/2017 | Guzman |
| 2018/0059003 A1 | 3/2018 | Jourdainne |
| 2018/0156718 A1 | 6/2018 | Fleisher et al. |
| 2018/0202918 A1 | 7/2018 | Tanaka et al. |
| 2018/0202923 A1 | 7/2018 | Kageyama et al. |
| 2018/0212396 A1 | 7/2018 | Kim |
| 2018/0214050 A1 | 8/2018 | Purves |
| 2018/0261974 A1 | 9/2018 | Purves et al. |
| 2018/0350304 A1 | 12/2018 | Ishii |
| 2019/0261891 A1 | 8/2019 | Ahmad et al. |
| 2019/0265159 A1 | 8/2019 | Koulikov |
| 2019/0265160 A1 | 8/2019 | Koulikov |
| 2019/0271641 A1 | 9/2019 | Koulikov |
| 2019/0301933 A1 | 10/2019 | Allison |
| 2019/0323955 A1 | 10/2019 | Koulikov |

FOREIGN PATENT DOCUMENTS

| | | |
|---|---|---|
| CA | 2997070 A1 | 9/2019 |
| CN | 101470072 A | 7/2009 |
| CN | 102316801 B | 1/2012 |
| CN | 102798631 A | 11/2012 |
| CN | 102841082 A | 12/2012 |
| CN | 102264292 B | 5/2014 |
| CN | 106877168 A | 6/2017 |
| CN | 106908389 A | 6/2017 |
| CN | 106981552 A | 7/2017 |
| CN | 107037003 A | 8/2017 |
| CN | 106981552 B | 4/2019 |
| CN | 109856054 A | 6/2019 |
| DE | 2130331 A1 | 3/1977 |
| DE | 2723939 A1 | 12/1978 |
| DE | 3819687 A1 | 12/1989 |
| DE | 10156149 A1 | 6/2003 |
| EP | 557658 A1 | 9/1993 |
| EP | 600711 A2 | 6/1994 |
| EP | 1535047 B1 | 6/2005 |
| EP | 1304955 B1 | 12/2008 |
| EP | 1997198 B1 | 6/2012 |
| EP | 1418842 B1 | 7/2012 |
| EP | 3037805 A1 | 6/2016 |
| EP | 2745097 B1 | 2/2018 |
| EP | 3419122 A1 | 12/2018 |
| EP | 3467473 A1 | 4/2019 |
| GB | 1019295 A | 2/1966 |
| IS | 20040190563 A1 | 9/2004 |
| JP | 2001194299 A | 7/2001 |
| JP | 2006189392 A | 7/2006 |
| JP | 2006226727 A | 8/2006 |
| JP | 2010243270 A | 10/2010 |
| JP | 2013011620 A | 1/2013 |
| JP | 5341519 B2 | 11/2013 |
| JP | 5537174 B2 | 7/2014 |
| JP | 2016503904 A | 2/2016 |
| WO | 2090935 | 11/2002 |
| WO | 2005038436 A2 | 4/2005 |
| WO | 2005076875 A2 | 8/2005 |
| WO | 2005088274 A1 | 9/2005 |
| WO | 2017142644 A1 | 12/2007 |
| WO | 2011117572 A1 | 9/2011 |
| WO | 2012004794 A1 | 1/2012 |
| WO | 2012059768 A1 | 5/2012 |
| WO | 2014062392 A1 | 4/2014 |
| WO | 2014070952 A1 | 5/2014 |
| WO | 2016061533 | 4/2016 |
| WO | 2017187120 A1 | 11/2017 |
| WO | 2018142027 A1 | 8/2018 |
| WO | 2019074922 A1 | 4/2019 |
| WO | 2019239827 A1 | 12/2019 |

OTHER PUBLICATIONS

Office Action for U.S. Appl. No. 16/564,662 dated Aug. 10, 2020.
Office Action for U.S. Appl. No. 16/509,207 dated Aug. 18, 2020.
Orr et al. "Cavity ringdown spectroscopy with widely tunable swept-frequency lasers," European Quantum Eletronics Conference, 2005 *EQEC '05) Jun. 12-17, 2005, p. 204.
ISR for PCT/CA2007/002306 dated Apr. 17, 2008.
Office action for CA2671122 dated Jun. 13, 2011.
Harren et al., Photoacoustic Spectroscopy in Trace Gas Monitoring, encyclopedia of Analytical Chemistry, pp. 2203-2226, J. Wiley and Sons, 2000.
Freed, C., Status of CO2 Isotope Lasers and Their Applications in Tumable Laser Spectroscopy, IEEE Journal of Quantum Electronics, vol. QE-18, No. 8, 1982.
Sharpe et al., "Gas Phase Databases for Quantitative Infrared Spectroscopy," Applied Spectroscopy, vol. 58, No. 12, 2004.
Akaike, H., "A new look at the statistical model identification," IEEE Transactions on Automatic Control, 19(6): 716-723, 1974.
Cormier, John G., "Development of an Infrared Cavity Ringdown Spectroscopy Experiment and Measurements of Water Vapor Continuum Absorption.," Thesis, 2002.
Kurochkin et al., "Three Mirror Cavity CO2 Lserfor Inactivity Saturated-Absorption Spectroscopy." Optical Spectroscopy, vol. 65, No. 2, pp. 265-267, Aug. 1988.
Office Action for U.S. Appl. No. 12/517,036 dated Dec. 14, 2011.
Fuchs, D., et al., "Decline of exhaled isoprene in lung cancer patients correlates with immune activation," Journal of breath research 6.2 (2012): 027101+B8.
Ligor, Magdalena, et al., "Determination of volatile organic compounds of exhaled breath of patients with lung cancer using solid phase microextraction and gas chromatography mass spectrometry," Clinical chemistry and laboratory medicine 47.5 (2009): 550-560.
Vaughan, Christina, et al., "Automated determination of seven phenolic compounds in mainstream tobacco smoke," Nicotine and Tobacco Research 10.7 (2008): 1261-1268.
Cope, et al., "Effects of ventilation on the collection of exhaled breath in humans," J. App I Physiol 96: 1371-1379: 2004.
Office action for U.S. Appl. No. 14/720,447 dated Apr. 6, 2017.
Office action for U.S. Appl. No. 14/720,447 dated Apr. 19, 2018.
Final office action for U.S. Appl. No. 14/720,447 dated Sep. 13, 2017.
English translation of DE102013215640A1.

(56) References Cited

OTHER PUBLICATIONS

Office action for U.S. Appl. No. 14/720,456 dated Jun. 14, 2017.
Office action for U.S. Appl. No. 15/920,212 dated Jun. 27, 2019.
Final Office action for U.S. Appl. No. 15/920,212 dated Oct. 3, 2019.
Notice of Allowance for U.S. Appl. No. 15/920,212 dated Jan. 23, 2020.
International Search Report and Written Opinion for PCT/CA2020/050252 dated May 12, 2020.
International Search Report and Written Opinion for PCT/CA2020/050250 dated May 22, 2020.
International Search Report and Written Opinion for PCT/CA2020/050/249 dated Apr. 29, 2020.
International Search Report and Written Opinion for PCT/CA2020/050248 dated Jun. 11, 2020.
Office action for U.S. Appl. No. 15/917,225 dated Mar. 9, 2020.
Office action for U.S. Appl. No. 15/917,225 dated May 14, 2020.
Written Opinion for PCT/CA2021/050092 dated Mar. 29, 2021.
International Search Report for PCT/CA2021/050092 dated Mar. 29, 2021.
Written Opinion for PCT/CA2021/050091 dated Apr. 6, 2021.
International Search Report for PCT/CA2021/050091 dated Apr. 6, 2021.
Written Opinion for PCT/CA2021/050090 dated Apr. 14, 2021.
International Search Report for PCT/CA2021/050090 dated Apr. 14, 2021.
Written Opinion for PCT/CA2021/050089 dated Apr. 7, 2021.
International Search Report for PCT/CA2021/050089 dated Apr. 7, 2021.
Written Opinion for PCT/CA2021/050087 dated Apr. 9, 2021.
International Search Report for PCT/CA2021/050087 dated Apr. 9, 2021.
Written Opinion for PCT/CA2021/051055 dated Oct. 26, 2021.
International Search Report for PCT/CA2021/051055 dated Apr. 26, 2021.
Office Action for U.S. Appl. No. 16/740,026 dated Jun. 4, 2021.
Office Action for U.S. Appl. No. 16/599,943 dated Aug. 12, 2021.
Office Action for U.S. Appl. No. 16/599,943 dated Dec. 3, 2021.
Office Action for U.S. Appl. No. 16/813,073 dated Oct. 6, 2020.

\* cited by examiner

SPECTROSCOPY SYSTEM AND METHOD OF PERFORMING SPECTROSCOPY

CROSS-REFERENCE TO RELATED APPLICATIONS

This application claims the benefit of U.S. Provisional Application No. 62/828,750, filed Apr. 3, 2019, the contents of which are incorporated herein by reference in their entirety.

FIELD

The specification relates generally to gaseous sample analysis, and, in particular, to a spectroscopy system and a method of performing spectroscopy.

BACKGROUND OF THE DISCLOSURE

Spectroscopy systems analyze the interaction between matter and radiation in order to learn about the matter. Generally, this analysis is used to classify the matter or constituents thereof according to previous baseline observations for known molecules. One such form of spectroscopy is cavity ring-down spectroscopy ("CRDS") that is generally used to identify and quantify a single analyte in a sample using their absorption spectra. A typical CRDS system employs a laser generating a beam that is directed into a cavity of a chamber having two highly reflective mirrors. The beam is normally within the visible light spectrum, or in the near infrared ("IR") spectrum, and is tuned to a single wavelength to identify the presence of a single molecule. The beam is then reflected repeatedly between the mirrors, which allow a fraction of the light to escape the ring-down cavity. When the laser is in resonance with a cavity mode, intensity builds up in the cavity due to constructive interference. When the light entering the cavity is extinguished, the intensity of the light in the ring-down cavity decays at a pre-determined rate. A small fraction of the light is not reflected by the mirrors and escapes the ring-down cavity. The intensity of the escaping light is measured by a sensor component to determine the decay rate.

When the gaseous sample is placed in the ring-down cavity, analytes present in the gaseous sample absorb some of the light, thereby accelerating the decay of the intensity of the light in the ring-down cavity. Absorption spectra are generated by measuring the decay times of the light in the presence of the gaseous sample at a plurality of specific wavelengths relative to the decay times of the light in the absence of the gaseous sample at these wavelengths. A linear regression of the measured absorption spectra for the gaseous sample with the known absorption spectra of various analytes or other suitable method enables the identification and quantification of individual analytes in the gaseous sample.

The loading of samples can be problematic. Traditional approaches for loading samples include coupling bags made of plastic or other materials to a CRDS system for analysis of a gaseous sample contained therein. Where a sample is of human breath, the sample can include $CO_2$ and water that can interfere with the spectroscopy of other substances contained in the breath sample due to the absorption characteristics of these molecules. This is particularly true when a laser having a wavelength in the infrared spectrum is employed, as water absorb light in this wavelength range. Further, $CO_2$ absorbs light at the wavelengths emitted by $CO_2$ lasers.

Another issue is that some of the constituents may adhere to the inside surfaces of spectroscopy systems, and may loosen during the loading of subsequent samples, thus contaminating those samples.

SUMMARY OF THE DISCLOSURE

In one aspect, there is provided a spectroscopy system, comprising: a resonant cavity; a first conduit configured to couple at a first end thereof to a gas source, and at a second end thereof to a first end of a collection medium containing a sample for analysis; and a second conduit configured to couple at a first end thereof to a second end of the collection medium, and at a second end thereof to the resonant cavity. The resonant cavity can be a ring-down cavity.

The collection medium can be a sorbent tube. A heater can be positioned to heat the sorbent tube when the sorbent tube is coupled to the first conduit and the second conduit.

The first end of the sorbent tube can be an exhaust end and the second end of the sorbent tube can be a sample-receiving end.

The gas source can provide gas at a source gas pressure above a target sample pressure within the resonant cavity for analysis of the sample.

The spectroscopy system can further include a pressure sensor positioned upstream of the sorbent tube when gas is flowing from the sorbent tube to the resonant cavity.

The spectroscopy system can further include a control system coupled to the pressure sensor to receive measured pressure therefrom, and to a valve controlling fluid communication between the gas source and the sorbent tube and the pressure sensor, the control system conditionable to a sample loading mode, in which the valve is repeatedly opened and closed to introduce more of the gas from the gas source until the measured pressure is at the target sample pressure.

The measured pressure can be compared to the target sample pressure when the valve is closed.

The valve can be a first valve, and the spectroscopy system can further comprise: a second valve positioned along the second conduit; a third conduit in fluid communication with the first conduit and in fluid communication with the second conduit at a position between the second valve and the sorbent tube; a third valve controlling fluid communication through the third conduit; a fourth conduit in fluid communication with the first conduit between the first valve and the sorbent tube; and a fourth valve positioned along the first conduit between the third conduit and the fourth conduit.

The pressure sensor can be positioned along the third conduit between the first conduit and the third valve.

The spectroscopy system can further include a fifth valve positioned along the second conduit between the third conduit and the sorbent tube.

The spectroscopy system can further include a sixth valve positioned along the first conduit between the sorbent tube and the fourth conduit.

The control system can be configured to operate in a first mode, wherein the control system opens the first valve, the third valve, and the fifth valve and closes the second valve and the fourth valve to flow gas through the sorbent tube and through the fourth conduit, and in a second mode, wherein the control system opens first valve, the fourth valve, the second valve, and the fifth valve and closes the third valve to flow gas through the sorbent tube and into the resonant cavity.

The spectroscopy system can further include a filter positioned along the second conduit.

In another aspect, there is provided a method of performing spectroscopy, comprising: coupling a gas source to a first end of a collection medium containing a sample for analysis; coupling a second end of the collection medium to a resonant cavity; and flowing gas from the gas source through the collection medium and into the resonant cavity. The resonant cavity can be a ring-down cavity.

The collection medium can be a sorbent tube. The method can include heating the sorbent tube to a target temperature.

The first end of the sorbent tube can be an exhaust end and the second end of the sorbent tube can be a sample-receiving end.

The method can further include measuring the pressure in the resonant cavity via a pressure sensor positioned upstream of the sorbent tube when gas is flowing from the sorbent tube to the resonant cavity.

The method can further include repeatedly opening and closing a valve controlling fluid communication between the gas source and the sorbent tube until the measured pressure matches a target sample pressure level.

The measured pressure can be compared to the target sample pressure level when the valve is closed.

The flowing gas can include flowing gas through the sorbent tube from a first end of the sorbent tube to a second sample-receiving end of the sorbent tube, and the method can further include flowing gas through the sorbent tube from the sample-receiving end thereof to the exhaust end thereof.

The method can include filtering the flowing gas before the flowing gas enters the resonant cavity.

In a further aspect, there is provided a spectroscopy system, comprising: a resonant cavity defined by at least one interior surface and having a first mirror positioned towards a first end thereof and a second mirror positioned towards a second end thereof, wherein the at least one interior surface is inert. The resonant cavity can be a ring-down cavity.

The spectroscopy system can further include a sample-loading system coupled to the resonant cavity and having at least one conduit therein extending between a sample source and the resonant cavity, wherein the conduit has an inert coating on an interior surface thereof.

The spectroscopy system can further include a sample-loading system coupled to the resonant cavity and having at least one conduit therein extending between the resonant cavity and an exhaust outlet, the at least one conduit having a valve positioned therealong, wherein a portion of the at least one conduit extending between the resonant cavity and the valve has an inert coating on an interior surface thereof.

The spectroscopy system can further include a filter positioned to filter a gas before the gas enters the resonant cavity.

Other technical advantages may become readily apparent to one of ordinary skill in the art after review of the following figures and description.

BRIEF DESCRIPTIONS OF THE DRAWINGS

For a better understanding of the embodiment(s) described herein and to show more clearly how the embodiment(s) may be carried into effect, reference will now be made, by way of example only, to the accompanying drawings in which.

Figure 1:
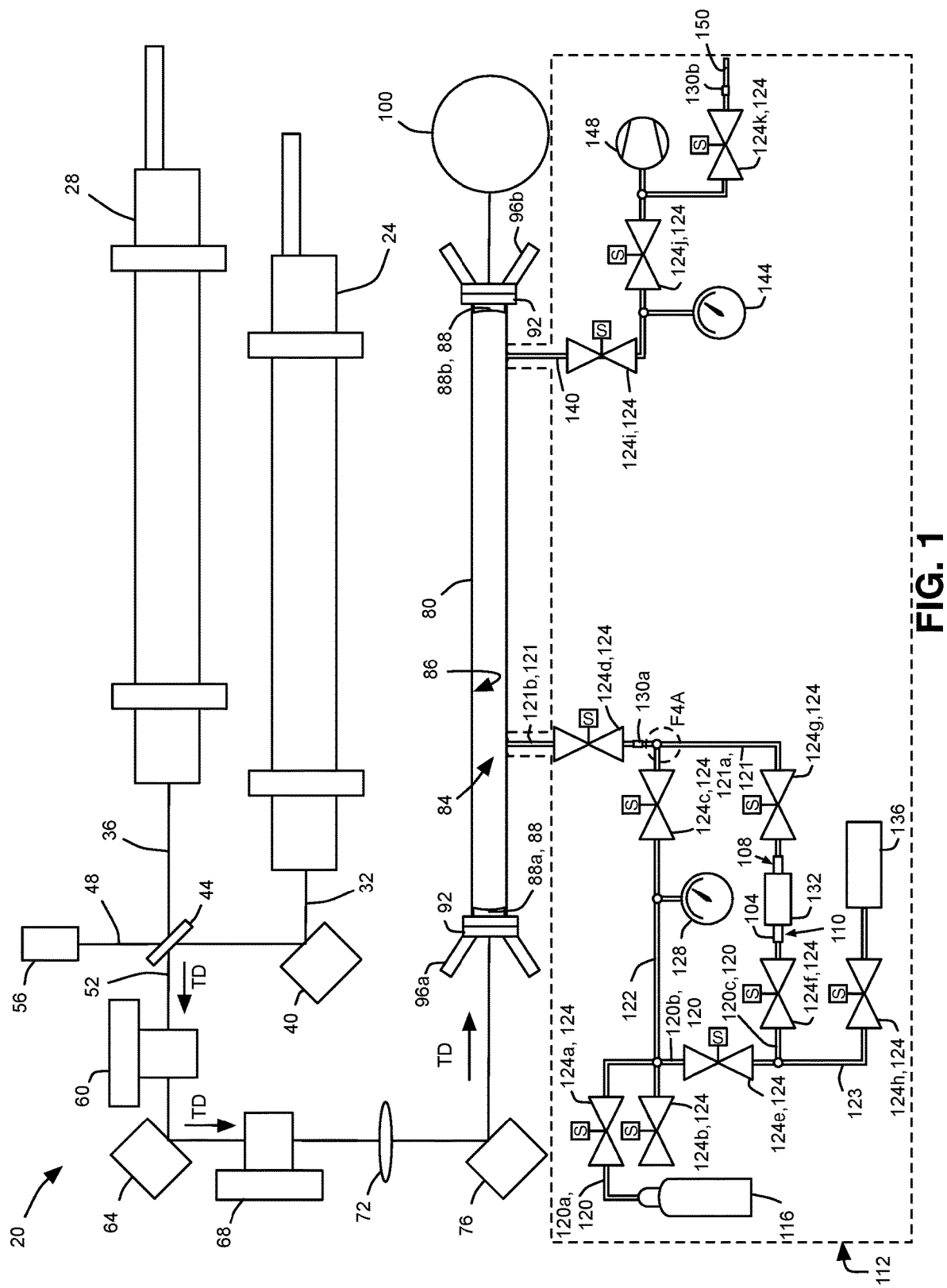
FIG. 1 is a schematic diagram of various optical and pneumatic components of a cavity ring-down spectroscopy system in accordance with one embodiment.

Unless otherwise specifically noted, articles depicted in the drawings are not necessarily drawn to scale.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiment or embodiments described herein. However, it will be understood by those of ordinary skill in the art that the embodiments described herein may be practiced without these specific details. In other instances, well-known methods, procedures and components have not been described in detail so as not to obscure the embodiments described herein. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

Various components of a spectroscopy system in accordance with a particular embodiment are shown in FIG. 1. In this embodiment, the spectroscopy system is a cavity ring-down spectroscopy ("CRDS") system 20, but could be any other suitable spectroscopy system, such as an electron spectroscopy system, an atomic spectroscopy system, etc. A $CO_2$ laser 24 and a carbon-13 $O_2$ laser 28 are provided. The $CO_2$ laser 24 and the carbon-13 $O_2$ laser 28 are gas tube lasers that emit at a series of quasi-evenly-spaced, well-known frequencies that can be rapidly selected using an adjustable diffraction grating apparatus. Gas tube laser technology has a long history and is a stable and robust way of generating infrared radiation at precisely-known frequencies. Both the $CO_2$ laser 24 and the carbon-13 $O_2$ laser 28 emit light in the mid-IR spectrum.

Each of the $CO_2$ laser 24 and the carbon-13 $O_2$ laser 28 has one or more piezos that move an output coupler to enable adjustment of the length of the laser cavity as well as an actuator to change the angle of grating at the back of the cavity, thereby changing its pitch to adjust which wavelengths it reflects. By both adjusting the length of the laser cavity and changing the angle of the grating, the laser can be very accurately tuned to a specific wavelength and desired mode quality.

The $CO_2$ laser 24 produces a first laser beam 32, and the carbon-13 $O_2$ laser 28 produces a second laser beam 36. Depending on the light frequency desired, either the $CO_2$ laser 24 is tuned and generates the first laser beam 32 while the carbon-13 $O_2$ laser 28 is detuned, or the carbon-13 $O_2$ laser 28 is tuned and generates the second laser beam 36 while the $CO_2$ laser 24 is detuned. In this manner, at most only one of the $CO_2$ laser 24 and the carbon-13 $O_2$ laser 28 outputs a beam at any particular time so that the first beam 32 and the second beam 36 are not combined simultaneously. Mid-infrared, and specifically long wavelength infrared, was chosen as the type of light as most volatile organic compounds absorb light in this range. As a result, multiple volatile organic compounds can be measured by a single system. $CO_2$ lasers operate in this range and have sufficient power and linewidth narrowness for ring-down spectroscopy. Using two lasers adds to the range and number of available wavelengths that the CRDS system 20 can use to analyze gaseous samples.

The first laser beam 32 is redirected via a mirror 40 on an optic mount towards a beam splitter 44. The beam splitter 44 is partially reflective and partially transmissive, and splits each of the first laser beam 32 and the second laser beam 36 into two beams, a sampling beam 48, and a working beam 52 that has the same characteristics as the sampling beam 48 and can be of similar intensity as the sampling beam 48.

The sampling beam 48 is received by a fast infrared detector 56. The fast infrared detector 56 measures the amplitude and the beat frequency of the sampling beam 48 using an oscilloscope. The beat frequency can indicate the presence of higher order modes resulting from a less-than-optimal tuning of the $CO_2$ laser 24 or the carbon-13 $O_2$ laser 28. In response to the detection of an undesirable beat frequency, the corresponding laser 24 or 28 is tuned until the amplitude of the beat frequency is minimized or eliminated while maximizing the intensity. If the amplitude of the beat frequency cannot be reduced below an acceptable level, the laser can be tuned to a different wavelength.

The working beam 52 continues to a first optical modulator 60, which then deflects the working beam 52 to a mirror 64 on an optic mount. The mirror 64 redirects the light towards a second optical modulator 68 that, in turn, deflects the working beam 52 to a focusing lens 72. The optical modulators are used to control the intensity of the light beam generated by the laser. In the present embodiment, the first and second optical modulators 60, 68 are acousto-optic modulators ("AOMs"), also referred to as Bragg cells. AOMs are one type of optical modulator that uses a piezoelectric transducer coupled to a material such as germanium or glass. In the described embodiment, the material is germanium. When an oscillating electric signal is applied to the piezoelectric transducer, the piezoelectric transducer vibrates, creating sound waves in the material. These sound waves expand and compress the material, thereby creating periodic variations in the refractive index and allowing for Bragg diffraction. Light entering the AOM at the first order Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively attenuating the light along the deflected optical path. A by-product of the AOM is that the frequency of the light being deflected is shifted.

In other embodiments, the optical modulators could alternatively be electro-optic modulators. An electro-optic modulator is another type of optical modulator that applies a DC or low-frequency electric field to a material to distort the position, orientation, and/or shape of the molecules of the material. As a result, the refractive index is altered to change the phase of the outgoing beam as a function of the applied field. By sending the beam through a polarizer, the phase modulation is converted to intensity modulation. In another method, a phase modulator when placed in a branch of an interferometer can act as an intensity modulator.

Further, while the CRDS system 20 is described as having two optical modulators, in other embodiments, the CRDS system can have fewer or a greater number of optical modulators.

The first and second optical modulators 60, 68 act as attenuators to adjust the intensity of the working beam 52 and extinguish the beam at the commencement of a ring-down event. A ring-down event includes the extinguishing of the working beam 52 illuminating a ring-down cavity or the detuning of the laser for the ring-down chamber, and the collection of light intensity data from the ring-down chamber. As they are AOMs, the first and second optical modulators 60, 68 use the acousto-optic effect to diffract the light using sound waves (normally at radio-frequency). In each of the first and second optical modulators, a piezoelectric transducer is coupled to a material such as germanium or glass, and an oscillating electric signal is used to cause the piezoelectric transducer to vibrate. The vibrating piezoelectric transducer creates sound waves in the material that expand and compress the material, thereby creating period variations in the refractive index and allowing for Bragg diffraction. Light entering the AOM at Bragg angle relative to the plane perpendicular to the axis of propagation of the acoustic wave will be deflected by an amount equal to twice the Bragg angle at maximum efficiency. Extinguishing the electric signal removes the Bragg diffraction properties of the material and causes the light to pass through undeflected, effectively extinguishing the light along the deflected optical path. Hence, the intensity of the sound can be used to modulate the intensity of the light in the deflected beam.

The intensity of the light deflected by each of the first and second optical modulators 60, 68 can be between about 85%, representing a maximum deflection efficiency of the optical modulators 60, 68, and an attenuation limit of each of the first and second optical modulators 60, 68 of about 0.1% or less of the input light intensity. When the acoustic wave applied to the germanium is turned off, the deflected beam loses about 30 dB, or 99.9% or more, of the previous intensity. The attenuation limit means the upper limit of how much of the input light intensity can be reduced by the optical modulator.

Optic modulators are asymmetrical in that, as a side effect, they Doppler-shift the frequency of light in a first mode when the input light is received at a first end thereof, and they Doppler-shift the frequency of light in a second mode that is counter to the first mode when the input light is received at a second end thereof and the attenuation power is the same. The Doppler shift of the frequency of the light is, however, in the same direction regardless of whether the light enters at a first end or at a second end.

Conventional CRDS systems use a single optical modulator and, as a result, have a working beam that is frequency shifted. These frequency shifts are generally small in relation to the frequency of the light, and can change the manner in which the light is absorbed by matter in the cavity, but this frequency shift can be compensated for during the analysis. If diffraction is towards the acoustic wave source of an AOM, the frequency shift is downwards, and if diffraction is away from the acoustic wave source, the frequency shift is upwards. As discussed, the effect is minimal.

The working beam 52 deflected by the second optical modulator 68 is focused via a focusing lens 72. As the laser beam, and thus the working beam 52, travels from the $CO_2$ laser 24 or the carbon-13 $O_2$ laser 28, it continues to diverge. The focusing lens 72 focuses the working beam 52 back down.

A mirror 76 on an optic mount thereafter redirects the working beam 52 towards a ring-down chamber 80. The two mirrors 64, 76 extend the length of the path of the working beam 52.

The ring-down chamber 80 is an elongated tube defining a resonant cavity referred to as a ring-down cavity 84 therein. A front cavity mirror 88a and a rear cavity mirror 88b (alternatively referred to herein as cavity mirrors 88) are positioned at longitudinal ends of the ring-down cavity 84. The cavity mirrors 88 are highly reflective, both to light directed to the cavity mirrors 88 from outside of the ring-down cavity 84 and directed to the cavity mirrors 88 within the ring-down cavity 84. As a result, a fraction of the working beam 52 is directed at the front cavity mirror 88a, about 0.1%, passes through the front cavity mirror 88a, and enters the ring-down cavity 84, and the majority of the working beam 52, about 99.9% is reflected back towards the mirror 76.

The cavity mirrors 88 are mounted on mirror mounts 92 that are actuatable to adjust the positioning and orientation of the cavity mirrors 88. In particular, the front cavity mirror 88a towards the front of the ring-down cavity 84 is mounted on a mirror mount 92 that is actuatable via three mechanized micrometers 96a. The rear cavity mirror 88b towards the rear of the ring-down cavity 84 is mounted on a mirror mount 92 that is actuatable via three piezoelectric micrometers 96b that can be manually adjusted for optical alignment or with a piezo that allows them to be adjusted further with the piezo driver. In alternative embodiments, the front cavity mirror 88a and the rear cavity mirror 88b can be actuated by any suitable means, such as via piezoelectric micrometers, mechanical micrometers, etc.

The angle of each of cavity mirror 88 can be changed so that they are sufficiently aligned so that when a light beam enters the ring-down cavity 84, the light beam does not deviate. If one of the cavity mirrors 88 is askew, then some of the light gets reflected to the side of the ring-down cavity 84, intensity of the light is lost, high-order modes result, amongst other things. The micrometers 96 can also be simultaneously tuned to change the length of the ring-down cavity 84 without affecting the angle alignment. This allows for the tuning of the ring-down cavity 84 so that the ring-down cavity 84 resonates at the frequency of the light that is entering the ring-down cavity 84.

The focusing lens 72 focuses the laser light to match the optical mode of the ring-down cavity 84, so that the minimum waist of the beam is positioned at the same place as or very close to the minimum beam waist of the ring-down cavity 84. The position of the focusing lens 72 can be adjusted to match the optical mode of a range of laser wavelengths.

A light sensor in the form of a liquid nitrogen-cooled detector 100 is positioned behind the rear cavity mirror 88b to receive light escaping through it. The liquid nitrogen-cooled detector 100 measures the intensity of the light that escapes the ring-down cavity 84. Other types of sensors for measuring the intensity of the escaping light can be used in place of the liquid nitrogen-cooled detector 100.

Samples are loaded into the ring-down cavity 84 from a sorbent tube. A sorbent tube is a collection medium for sampling gases and vapors. Sorbent tubes are typically made of glass or stainless steel and can contain various types of solid adsorbent material ("sorbents"). Typical sorbents can include activated charcoal, silica gel, and organic porous polymers. The sorbents in the sorbent tube can be selected based on their ability to capture compounds of interest, do not react with the compounds of interest, and then allow the captured compounds to be desorbed for analysis. In this embodiment, the sorbent tube is a thermal desorption tube 104 that is used to collect the gaseous samples for testing. Thermal desorption tubes are generally made of stainless steel and contain various types of solid adsorbent material. Heat can be used to free the captured compounds of interest from the sorbents in the thermal desorption tube. Sorbent tubes are intended to be used by collecting in one direction and desorbing in the opposite. The sorbent material is typically more concentrated towards a sample-receiving end of the sorbent tubes. Also, some sorbent tubes have more than one sorbent, in which case it can be desirable to have the different sorbents in a specific order, and to adsorb and desorb the sorbent tubes in a particular direction.

An advantage of sorbent tubes is that they enable samples to be concentrated. Where, for example, the sample is a breath sample, the sorbent tube can be designed so that the sample contains a higher concentration of certain molecules of interest that are larger relative to other molecules that are smaller. By being designed particularly to trap larger molecules, the concentration of the larger molecules to the smaller molecules can be increased, thus improving analysis of the breath sample. The concentration feature of the CRDS system 20 is particularly advantageous where more than one analyte, and in particular one known analyte, is being analyzed in the sample. Where analysis of the sample is being performed to analyze the spectra as a whole and not just those portions of the spectra for a particular analyte, it is desirable to filter out other constituents that can dominate or overwhelm the measured spectrum and reduce the accuracy of the results.

In other embodiments, other types of sorbent tubes and other collection media can be employed.

In a particular example, the samples are human breath samples collected from patients. During sample collection, a person breathes into a sample-receiving end 108 of the thermal desorption tube 104 to capture breathe-borne molecules for testing and a part of the human breath is expelled via an exhaust end 110 of the thermal desorption tube. Human breath includes various constituents, including carbon dioxide, oxygen, and water molecules, and other larger molecules. These larger molecules contain compounds of interest that are generally trapped closer to the sample-receiving end 108 and the smaller molecules, such as carbon dioxide, oxygen, and water, are either more evenly distributed, are more concentrated towards the exhaust end, or pass right through the sorbent tube. As a result, compounds of interest are more concentrated towards the sample-receiving end 108 of the thermal desorption tube 104. In other applications, samples can be collected via one or both ends 108, 110 of the thermal desorption tube 104.

A pneumatic sample loading system 112 is used to load samples from thermal desorption tubes 104 into the ring-down cavity 84, and evacuate the sample loading system 112, including the ring-down cavity 84. During loading of a sample, the sample loading system 112 fills the ring-down cavity 84 with the sample that has been collected (i.e., to desorb the gaseous sample from the thermal desorption tube 104, get the gaseous sample into the ring-down cavity 84 without introducing contaminants), brings the pressure and temperature in the ring-down cavity to a target sample pressure of one atmosphere and 50 degrees Celsius, and seals the ring-down cavity 84. In this embodiment, the absorption spectra for a set of samples to which the measured absorption spectra are compared are determined at this pressure and temperature to ensure consistency between these parameters which can affect the results. In other embodiments, however, the target sample pressure and temperature can be fixed at other levels for the known and measured absorption spectra. During evacuation of a sample, the sample loading system 112 cleans the previously provided sample from the ring-down cavity 84 and the various conduits for guiding samples from the thermal desorption tube 104 to the ring-down cavity 84.

The sample loading system 112 has an intake portion that includes a nitrogen gas source 116. While, in this embodiment, the gas source is a nitrogen gas source, in other embodiments, the gas source can be any other source of a suitable gas. The nitrogen gas source 116 is a supply of gas in the form of a very clean nitrogen gas that is pressurized or that can pressurize the nitrogen gas to at least above one atmosphere of pressure. In the present embodiment, the nitrogen gas source 116 has a source gas pressure of at five psi above ambient pressure, but can be varied as long as the compression is sufficient to pressurize the ring-down cavity 84 to the target sample pressure of one atmosphere, or some other selected atmospheric pressure at which the analyses are run. In the illustrated embodiment, the nitrogen gas source 116 is the nitrogen gas that evaporates off a liquid nitrogen reservoir. The nitrogen gas source 116 is in fluid communication with a gas supply conduit 120 which is, in turn, in fluid communication with the thermal desorption tube 104. A gas intake valve 124a is positioned along a gas intake line 120a of the gas supply conduit 120. An auxiliary gas intake valve 124b enables connection of other gases, but is not regularly employed. The gas intake and auxiliary gas intake valves 124a, 124b are in communication with a gas intake line 120a that is, in turn, coupled to a pathing line 120b of the gas supply conduit 120.

The thermal desorption tube 104 is positioned within a heater 132 that can heat the thermal desorption tube 104 to free the sample from the sorbent of the thermal desorption tube 104. The heater 132 can be positioned to heat the entire thermal desorption tube or, alternatively, can be positioned to only heat a portion of the thermal desorption tube where the sorbent material is located. While the sample-receiving end 108 and the exhaust end 110 of the thermal desorption tube 104 are shown extending out of the heater 132 in FIG. 1, in other embodiments, the heater 132 can cover more or less, or all of the thermal desorption tube 104.

A pathing valve 124e is positioned along the pathing line 120b, which is in fluid communication with a tube exhaust line 120c of the gas supply conduit 120. The pathing valve 124e enables or disables direct access to the tube exhaust line 120c. The tube exhaust line 120c is in fluid communication with the exhaust end 110 of the thermal desorption tube 104. The tube exhaust line 120c includes a fore tube isolation valve 124f. The gas supply conduit 120 thus extends between the gas supply 116 and the thermal desorption tube 104.

A sample supply conduit 121 is in fluid communication with the sample-receiving end 108 of the thermal desorption tube 104 and the ring-down cavity 84. A rear tube isolation valve 124g is positioned along an initial portion 121a of the sample supply conduit 121. A cavity inlet valve 124d is positioned along a secondary portion 121*b* of the sample supply conduit 121. A filter 130*a* is positioned along the secondary portion 121*b* of the sample supply conduit 121 in front of a cavity inlet valve 124*d*. The sample supply conduit 121 thus extends between the thermal desorption tube 104 and the ring-down cavity 84. The filter 130*a* inhibits the entry of contaminants such as aerosols into the ring-down cavity 84 where they can deposit on the cavity mirrors 88 and interfere with reflection, and can degrade the light intensity in the ring-down cavity, such as by scattering by the aerosol particles.

A bypass conduit 122 is in fluid communication with the gas supply conduit 120 and the sample supply conduit 121. A pressure sensor 128 is positioned along the bypass conduit 122. A bypass conduit valve 124*c* is positioned along the bypass conduit 122 between the pressure sensor 128 and the sample supply conduit 121.

A tube exhaust conduit 123 is in fluid communication with the tube exhaust line 120*c* of the gas supply conduit 120 between the pathing valve 124*e* and the fore tube isolation valve 124*f*. The tube exhaust conduit 123 includes a sample exhaust valve 124*h* and a mass flow controller 136.

The sample loading system 112 also has an evacuation subsystem for evacuating samples and gases from the ring-down cavity 84. The evacuation subsystem includes an evacuation conduit 140 in fluid communication with the ring-down cavity 84. A cavity outlet valve 124*i* is positioned along the evacuation conduit 140. A pressure sensor 144 is positioned along the evacuation conduit 140 between the cavity outlet valve 124*i* and a vacuum cutoff valve 124*j*. A vacuum pump 148 is positioned along the evacuation conduit 140 and is separated from the pressure sensor 144 by the vacuum cutoff valve 124*j*. The vacuum pump 148 provides an exhaust outlet for the sample-loading system 112. A vacuum intake valve 124*k* is positioned along a pump intake line 150 that is in fluid communication with the evacuation conduit 140 between the vacuum cutoff valve 124*j* and the vacuum pump 148. An opposite end of the pump intake line 150 past the vacuum intake valve 124*k* is in fluid communication with ambient air. A filter 130*b* is positioned on the pump intake line 150 between the vacuum intake valve 124*k* and the opposite end of the pump intake line 150 to inhibit entry of contaminants in the pump intake line 150 that can interfere with the working of the vacuum pump 148.

Valves 124*a* to 124*k* may be alternatively referred to herein as valves 124.

While the sample supply conduit 121 and cavity inlet valve 124*d*, and the evacuation conduit 140 and the cavity outlet valve 124*i* are shown for convenience coupled to the ring-down cavity 84 at certain locations, it will be understood that the locations at which the conduits 121, 140 and valves 124*d*, 124*i* are coupled to the ring-down cavity 84 may vary. In a preferred configuration, the sample supply conduit 121 is in communication with the ring-down cavity 84 towards an end thereof adjacent the front cavity mirror 88*a* and the evacuation conduit 140 is in communication with the ring-down cavity 84 towards an end thereof adjacent the rear cavity mirror 88*b*.

Figure 2:
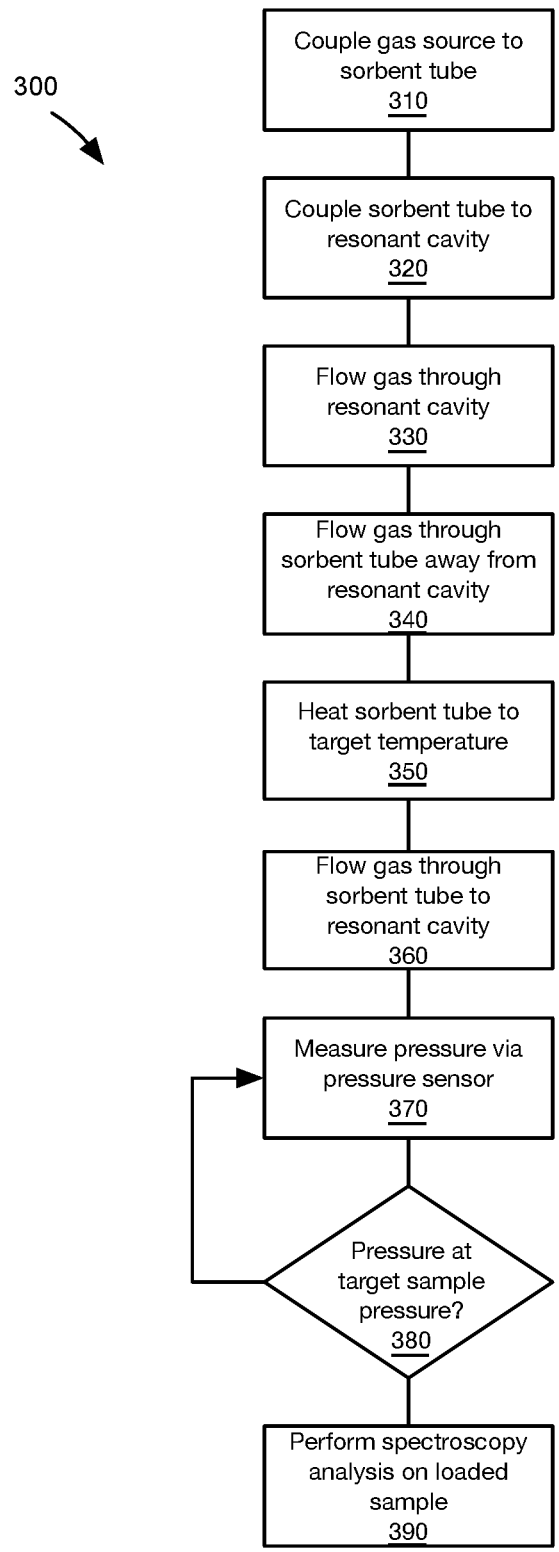
FIG. 2 is a flow chart of the general method of performing spectroscopy using the system of FIG. 1.

FIG. 2 shows a method of performing spectroscopy with the spectroscopy system of FIG. 1 generally at 300. Referring to FIGS. 1 and 2, when a new sample is to be loaded into the ring-down cavity 84, the thermal desorption tube 104 containing the new sample is coupled to the sample loading system 112. In particular, a sorbent tube is coupled to the gas source (310) and to a resonant cavity (320). The sorbent tube in the described embodiment is the thermal desorption tube 104 and the resonant cavity is the ring-down cavity 84. The thermal desorption tube 104 is removable and recouplable to enable different thermal desorption tubes containing different samples to be loaded.

Figure 3A:
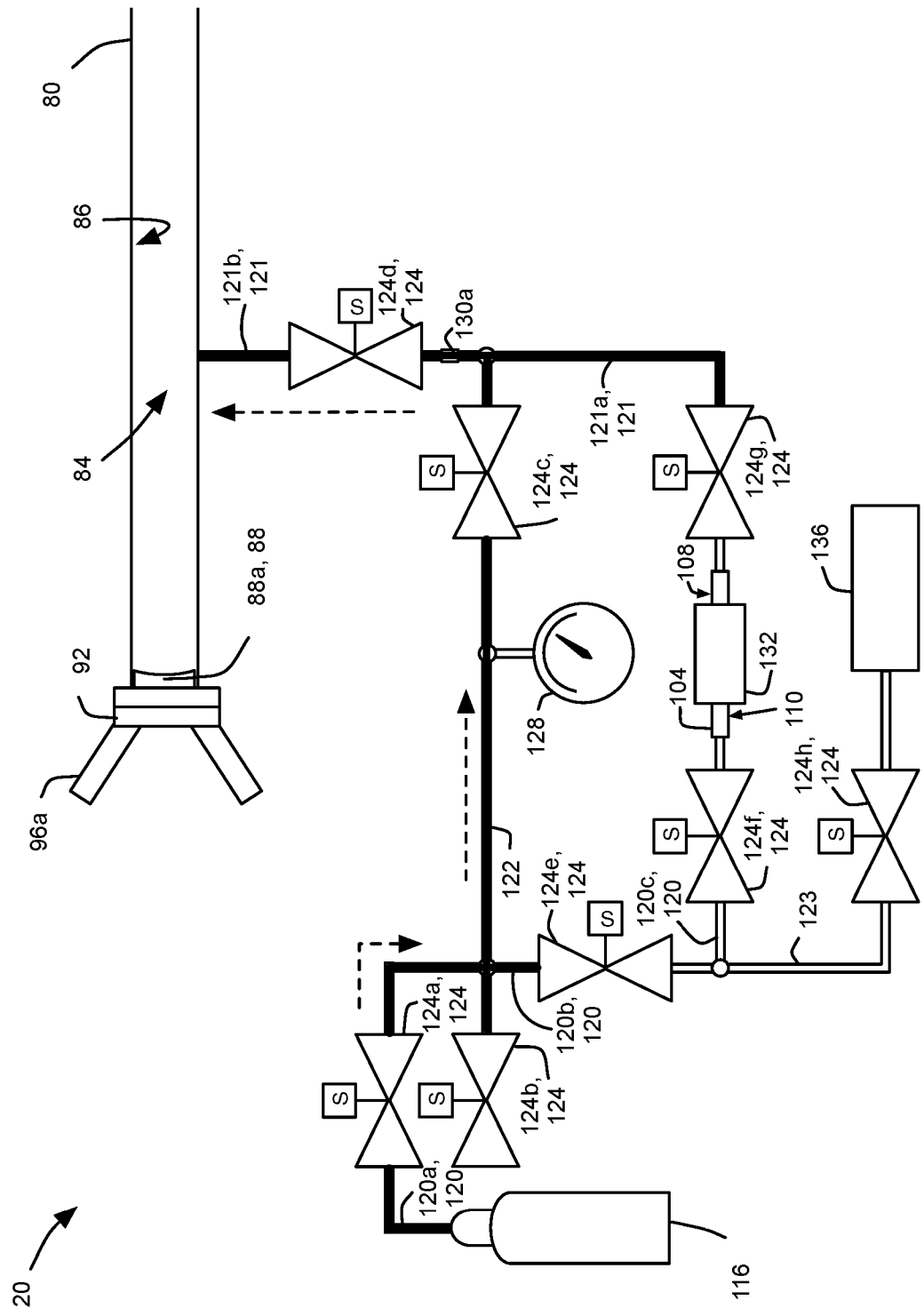
FIG. 3A is a schematic diagram of some of the pneumatic components shown in FIG. 1 with a flow of nitrogen gas during filling/evacuation of the ring-down cavity indicated.

During an evacuation phase, gas is flown through the resonant cavity (330). The vacuum intake valve 124*k* is opened and the vacuum pump 148 is turned on. The vacuum intake valve 124*k* is then closed, and the vacuum cutoff valve 124*j*, the cavity outlet valve 124*i*, the cavity inlet valve 124*d*, the bypass conduit valve 124*c*, and the pathing valve 124*e* are opened in succession. The contents of the lines along this path and the ring-down cavity 84 are evacuated from the CRDS system 20 by the vacuum pump 148. The pressure sensor 144 enables the determination of when the system has been evacuated sufficiently, especially when the pressure sensor 128 is cut off from the vacuum pump 148. When it is determined that the sample loading system 112 and the ring-down cavity 84 have been evacuated sufficiently, these same open valves 124*j*, 124*i*, 124*d*, 124*c*, and 124*e* are then closed in the reverse order. Thereafter, during a nitrogen fill phase, valves 124*a*, 124*c*, 124*d*, 124*i*, and 124*j* are opened to allow nitrogen gas from the nitrogen gas source 116 to fill the lines 120*a*, 122, and 121, as is shown in FIG. 3A. As will be understood, the evacuation conduit 140 shown in FIG. 1 is also filled with nitrogen gas. At the same time, the pathing valve 124*e* and the rear tube isolation valve 124*g* are in a closed state. The nitrogen gas is then purged using another evacuation phase. The nitrogen fill phase and the evacuation phase can be repeated as desired to clear out the lines. The CRDS system 20 is thus evacuated of the previously tested sample.

Figure 3B:
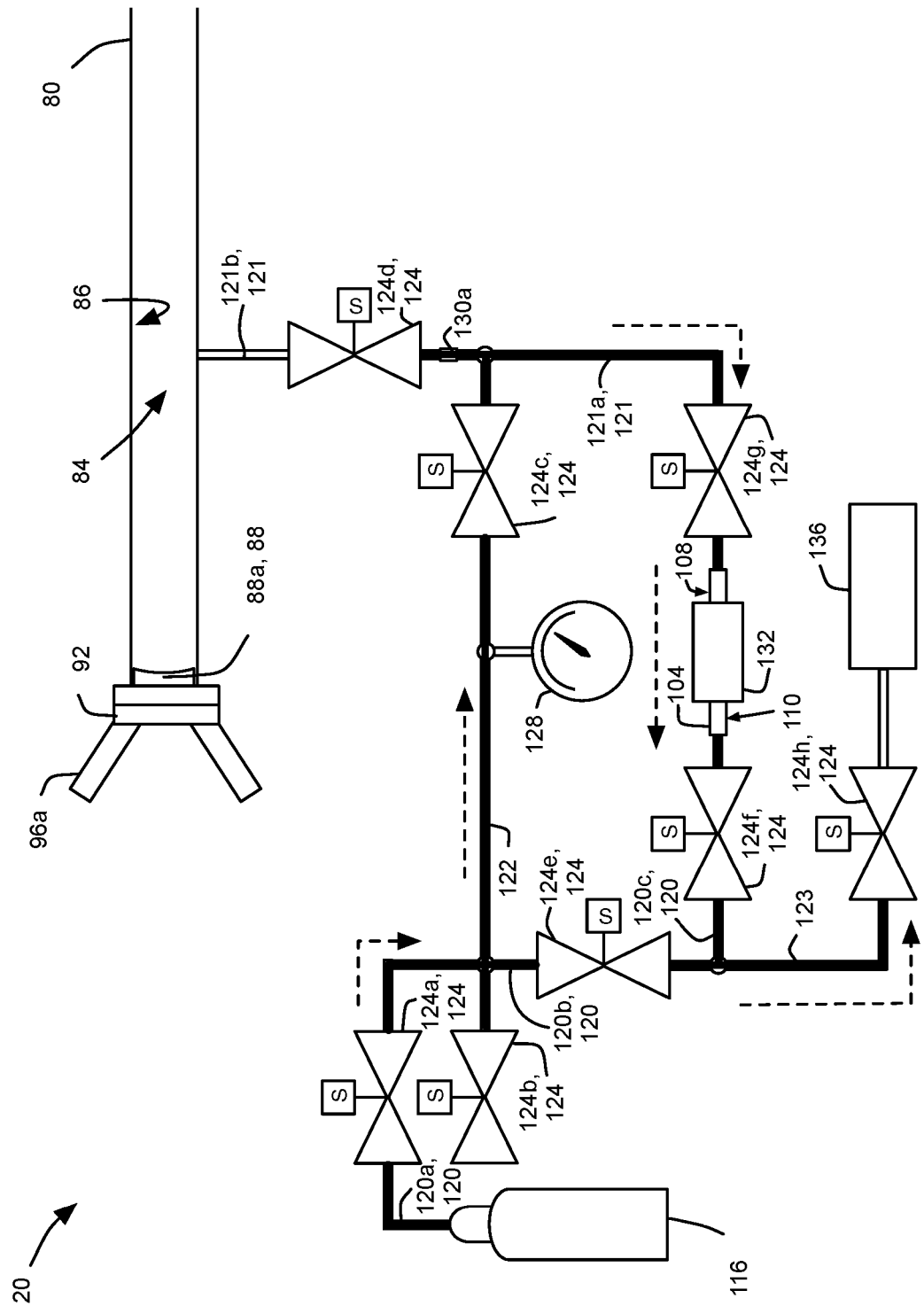
FIG. 3B is a schematic diagram of some of the pneumatic components shown in FIG. 1 with a flow of nitrogen gas during discharge of water and/or carbon dioxide indicated.

Next, gas is flown through the sorbent tube away from the resonant cavity (340). During the loading of the new sample, the thermal desorption tube 104 is flushed to remove carbon dioxide and water out of the thermal desorption tube 104 so that the amount of carbon dioxide and water loaded into the ring-down cavity 84 is minimized. In order to flush the thermal desorption tube 104, the gas intake valve 124*a*, the bypass conduit valve 124*c*, the rear tube isolation valve 124*g*, the fore tube isolation valve 124*f* and the sample exhaust valve 124*h* are opened to give a path to the nitrogen gas to forward flush the thermal desorption tube 104. At the same time, the pathing valve 124*e* and the cavity inlet valve 124*d* are in a closed state to direct the flow of nitrogen as shown in FIG. 3B. The thermal desorption tube 104 is selected to inhibit the collection of carbon dioxide and water with the gaseous sample, but there is still typically some carbon dioxide and water in the thermal desorption tube 104.

500 ml of nitrogen gas is put through the thermal desorption tube 104 to get out carbon dioxide and water that have remained in the thermal desorption tube 104 from the original sample. The mass flow controller 136 allows the nitrogen gas and borne carbon dioxide and water to be released at a specified flow rate. In the present configuration, this flow rate is 500 ml/min. All the valves 124 are then closed.

Once the carbon dioxide and the water have been removed from the thermal desorption tube 104, the sample loading system 112 is evacuated again using the same process discussed above to remove the nitrogen gas just introduced in the sample loading system 112 lines.

The sample loading system 112 can thus remove as much of the carbon dioxide and the water from the sample in the thermal desorption tube 104 as possible before the sample is loaded into the ring-down cavity 84. This is of particular interest because water and carbon dioxide absorb mid-infrared and long wave infrared wavelengths as may be generated by the lasers 24, 28.

The heater 132 surrounding the thermal desorption tube 104 then heats the thermal desorption tube 104 to the target temperature to thermally desorb the sample within the thermal desorption tube 104 (350).

Figure 3C:
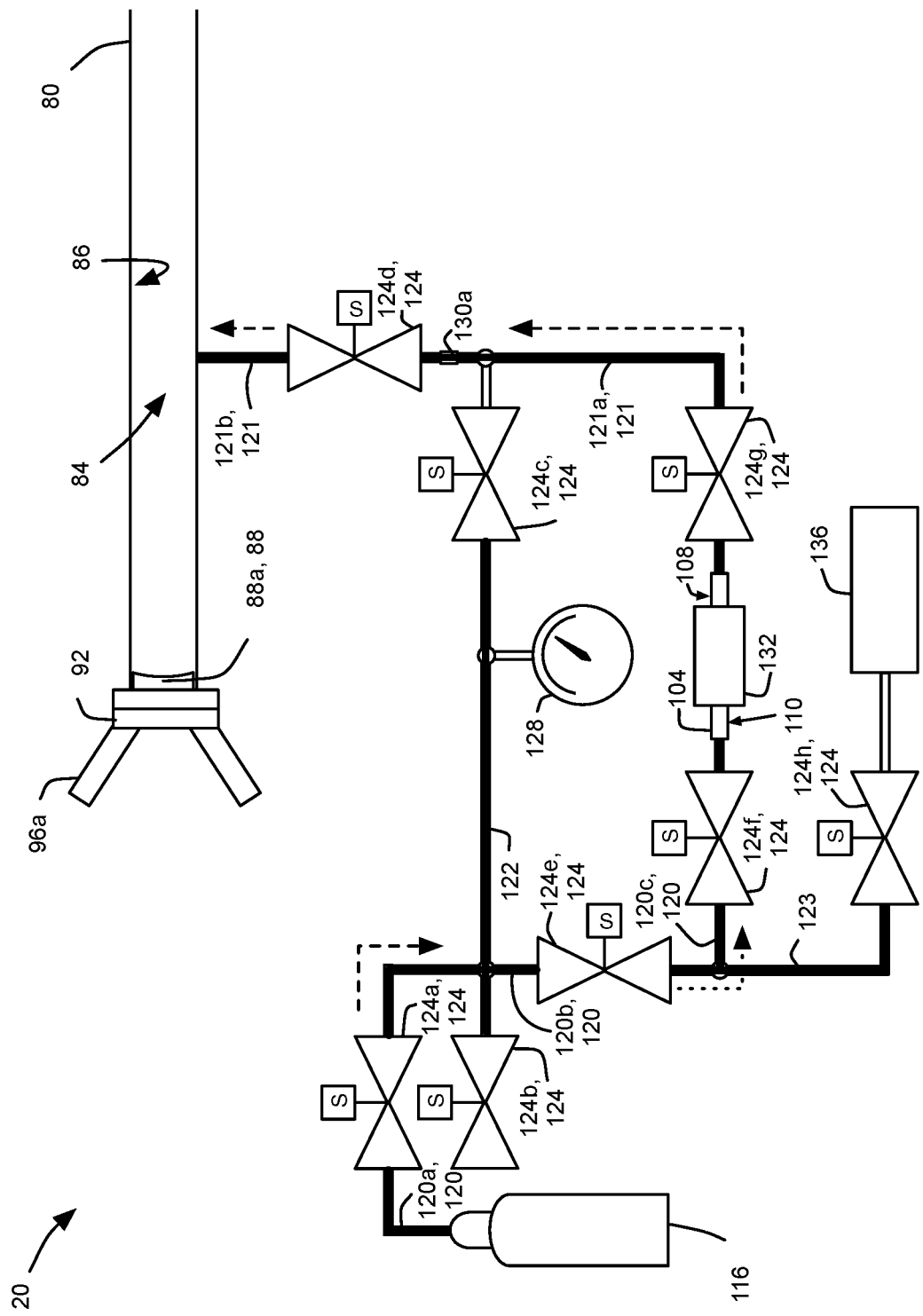
FIG. 3C is a schematic diagram of some of the pneumatic components shown in FIG. 1 with a flow of nitrogen gas during loading of a sample from the sorbent tube indicated.

Gas is flowed through the sorbent tube to the resonant cavity (360). Upon sufficient warming of the thermal desorption tube 104, the CRDS system 20 switches to a sample loading mode. The gas intake valve 124a, the pathing valve 124e, the fore tube isolation valve 124f, the rear tube isolation valve 124g, and the cavity inlet valve 124d are then opened to provide a direct path for the nitrogen gas from the nitrogen gas source 116, through the thermal desorption tube 104 having desorbed compounds of interest, and to the ring-down cavity 84. Concurrently, the bypass conduit valve 124c, the sample exhaust valve 124h, and the cavity outlet valve 124i are closed to force the nitrogen gas along the path as shown in FIG. 3C.

The pressure is then measured via a pressure sensor (370). It is desired to achieve a target sample pressure of one atmosphere within the ring-down cavity 84 as all of the reference data collected and analyzed is at this pressure level, thereby ensuring that the results are repeatable.

In the illustrated and described embodiment, the gas intake valve 124a is toggled open and closed by the system. The system waits for pressure to equalize in the ring-down cavity 84 and the conduits in fluid communication with it along which the pressure sensor 128 is located. The pressure sensor 128 is located upstream of the thermal desorption tube 104 when valves 124a, 124e, 124f, 124g, and 124d are opened, and valves 124c and 124h are closed, thereby preventing its contamination by the sample. As a result, it can take a short period of time for the pressure to equalize between the ring-down cavity 84 and the pressure sensor 128, particularly as the sorbent tube allows gas to flow through it at a restricted rate, thereby slowing the equalization process. In other embodiments, other types of valves can be employed, such as a throttle valve.

It is then determined if the pressure is at the sample target pressure (380). If, upon stabilization of the pressure sensor 128, the pressure reading is below the target sample pressure of one atmosphere, the gas intake valve 124a is toggled open and closed again to repeat the process until the pressure reading of the pressure sensor 128, after equalization, is at or sufficiently close to the target sample pressure of one atmosphere. When the pressure sensor 128 shows that the pressure level in the ring-down cavity 84 is at or sufficiently close to the target sample pressure, the valves, in particular at least valves 124a and 124d, are closed.

Upon achieving or substantially achieving the target sample pressure, spectroscopy analysis is performed on the sample, as is described below (390).

If it is desired to desorb at multiple temperatures, the vacuum intake valve 124k is opened, the vacuum pump 148 is turned on, the vacuum intake valve 124k is closed again, and the vacuum cutoff valve 124j and the cavity outlet valve 124i are opened in succession to evacuate the ring-down cavity 84. Then the cavity outlet valve 124i is closed before the desorption process is repeated.

A full evacuation is generally not performed between multiple desorptions as there is still some of the sample along the sample supply conduit 121 between the rear tube isolation valve 124g and the cavity inlet valve 124d that would be otherwise lost.

By pressurizing a fixed volume ring-down cavity containing the gaseous sample to a desired pressure level in this manner, the surface area within the ring-down cavity to which compounds can adhere can be decreased in comparison to variable volume ring-down cavities that may be used to raise the pressure within the cavity to the desired level.

The conduits 120, 121, 122, and 123, the valves 124, and the ring-down cavity 84 have an interior surface that is inert. Referring again to FIG. 1, an inert coating 86 is shown applied to the interior surface of the ring-down cavity 84. The inert coating 86 can be made of any suitably inert substance, such as a silica-based or quartz material.

Figure 4B:
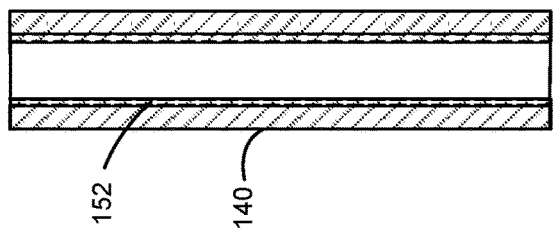
FIG. 4B is a section view of the evacuation conduit between the ring-down cavity and the cavity outlet valve of the pneumatic components of the cavity ring-down spectroscopy system of FIG. 1.
Figure 4C:
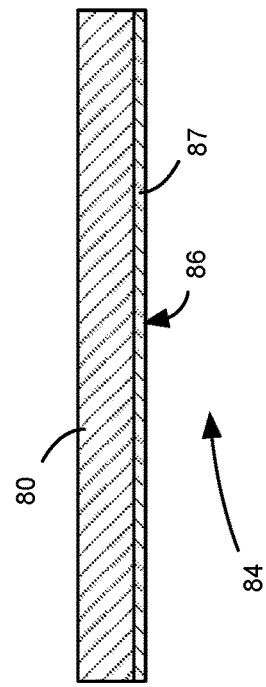
FIG. 4C is a section view of a portion of the ring-down chamber of the CRDS system of FIG. 1, wherein an inert coating is placed on the interior surface of the ring-down chamber defining the ring-down cavity.
Figure 4A:
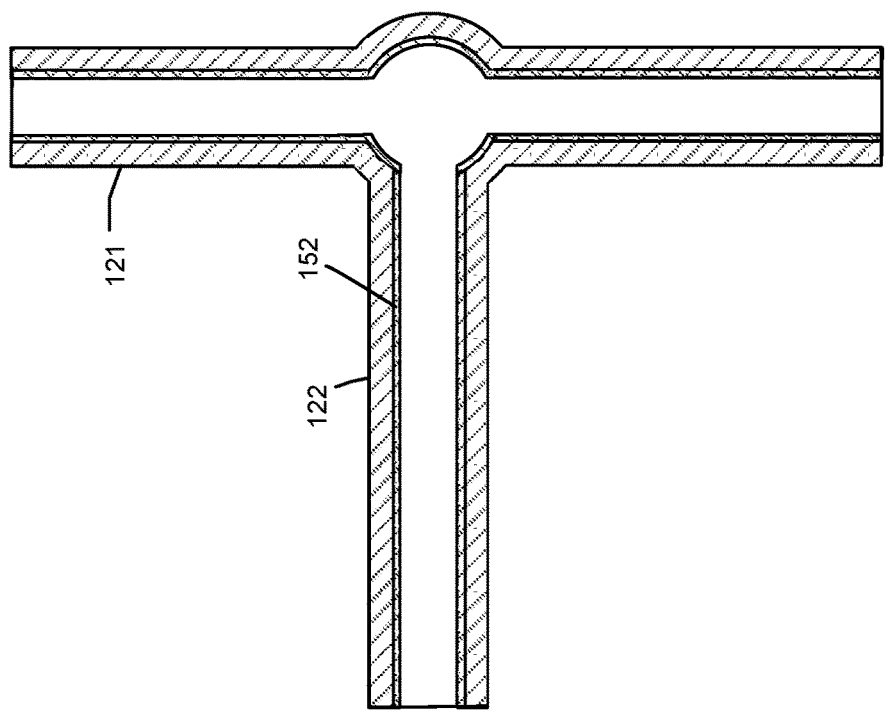
FIG. 4A is a section view of the region F4A of the pneumatic components of the cavity ring-down spectroscopy system of FIG. 1.

FIG. 4A shows a portion of the sample loading system 112 where the sample supply conduit 121 meets the bypass conduit 122. The conduits 121, 122 have an inert coating 152 on the inner or interior surface thereof. For example, the inert coating can be made of a silica-based material. Further, the interior surface of each of the valves 124 is inert. For example, the valves 124 can employ FKM, such as Viton, for the seals. In alternative implementations, the valves can use copper crush rings or the like.

FIG. 4B shows a portion of the evacuation conduit 140 between the ring-down cavity 84 and the cavity outlet valve 124i. The interior surfaces of the evacuation conduit 140 and the cavity outlet valve 124i are coated with an inert coating 152, such as a silica-based material. The cavity outlet valve 124i can employ FKM, such as Viton, for the seals. In alternative implementations, the valves can use copper crush rings or the like. As any molecules present in the evacuation conduit and the cavity outlet valve 124i can possibly travel back into the ring-down cavity 84, it is desirable to reduce the possibility of such molecules adhering to the interior surfaces of these elements.

FIG. 4C shows a portion of the ring-down chamber 80 having an interior surface 87 that defines the ring-down cavity 84. The inert coating 86 provides the interior surface 87 of the ring-down chamber 80.

The use of inert materials on the interior surfaces of the sample loading system 112 and the ring-down cavity 84 reduces the amount of the sample that remains in the ring-down cavity 84, conduits 120, 121, 122, valves 124, etc. As a result, prior analyzed samples will be less likely to adhere to surfaces within the sample loading system 112 and the ring-down cavity 84, and, thus, less likely to contaminate subsequent sample results by loosening and being analyzed with the subsequent samples.

Figure 5:
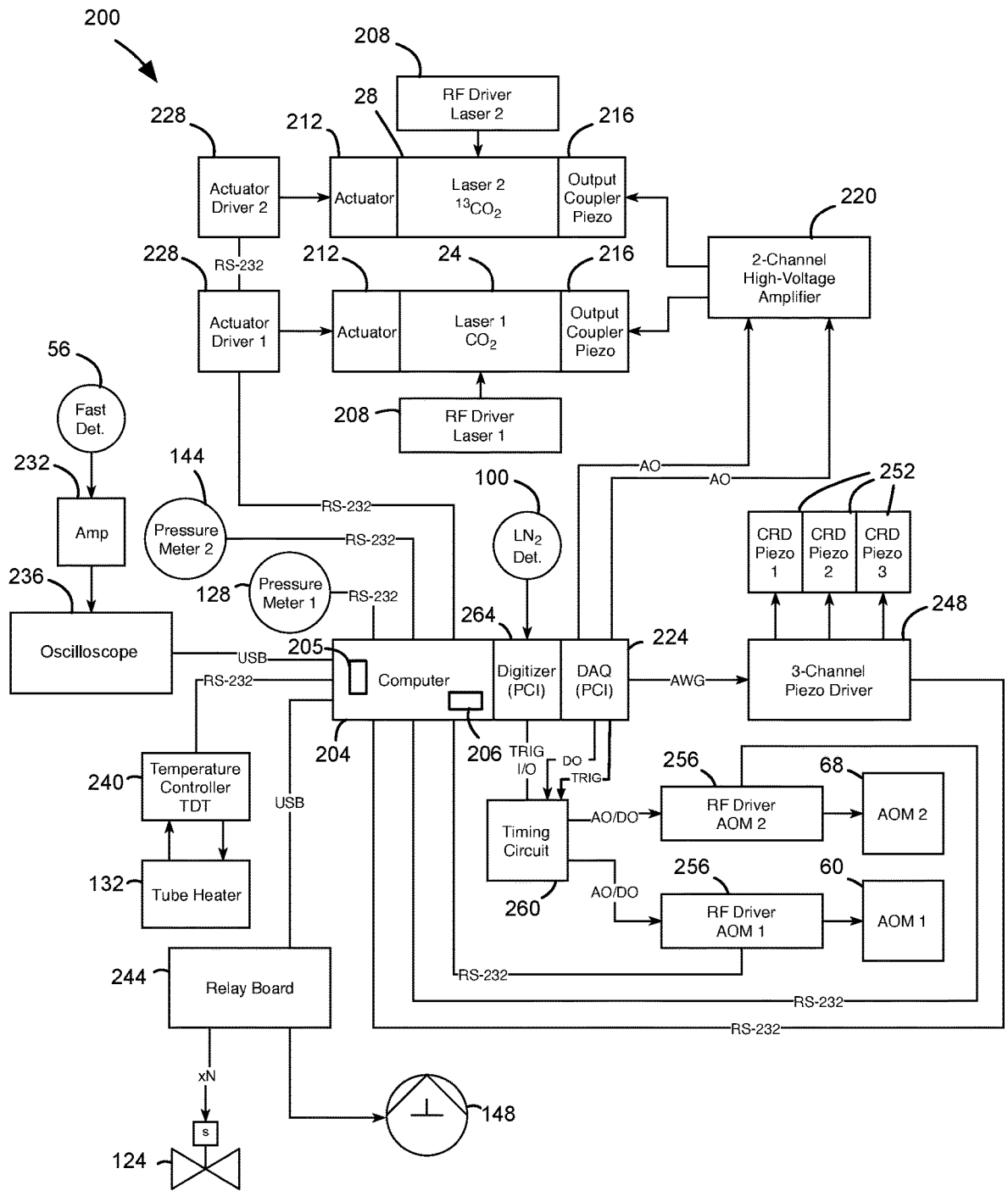
FIG. 5 is a schematic diagram of an electrical control system for controlling the various optical and pneumatic components of the cavity ring-down cavity ring-down system shown in FIG. 1.

FIG. 5 is a schematic diagram of an electronic control subsystem 200 for various components of the CRDS system 20 that are also illustrated. All of the lines represent electrical or electronic signals, with arrows representing unidirectional communications, setting of a voltage, etc., and lines that are not arrows representing bidirectional communications.

A computer 204 including one or more processors acts as a control module that controls the function of the various components illustrated in FIGS. 1 and 3A to 3C. The computer 204 has one or more processors 205 and storage 206 storing computer-executable instructions that, when executed by the processor 205, cause the processor 205 to direct the other components of the CRDS system 20 as described herein.

A pair of RF drivers 208 send approximately 40 MHz signal to power the $CO_2$ laser 24 and the carbon-13 $O_2$ laser 28. Each of the lasers 24, 28 is tuned using an output coupler and a diffraction grating. A grating actuator 212 actuates (turns) the diffraction grating. Another actuator actuates (translates) the output coupler. Each output coupler is driven by a 1000V output coupler piezo 216. A two-channel high-voltage amplifier 220 that powers the output coupler piezos 216 is adjustable between 0V and 1000V. The high-voltage amplifier 220 is set with an analog output signal from a data acquisition ("DAQ") card 224 in the computer 204. The DAQ generates output between 0V and 10V, and the high-voltage amplifier 220 multiplies the signal by 100 to generate a signal of 0V to 1000V to power the output coupler piezo 216. Each grating actuator 212 that changes the angle for the grating is driven by an actuator driver 228 that is given instructions by the computer 204 via RS-232. Each grating actuator 212 is moved so many millimeters, which is translated into a pitch angle of the laser 24, 28.

Data signals from the pressure sensors 128, 144 of the sample loading system 112 are received through RS-232.

The fast infrared detector 56 is connected to a small amplifier 232 and an oscilloscope 236 that can be used to read the amplitude and frequency of the beat signal that is used to tune the lasers 24, 28.

A temperature controller 240 for the thermal desorption tube heater 132 is controlled via RS-232 by the computer 204. The tube heater 132 includes a temperature sensor and a piece of aluminum that has heating tape wrapped around it. The heating tape and the temperature sensor are both connected to the temperature controller 240 which is a PID (proportional integral derivative) controller. The controller sets and reads back the temperature via RS-232 to the main computer 204.

A relay board 244 is connected to the computer 204 and is used to turn on and off each of the solenoid valves 124 and the vacuum pump 148.

A three-channel piezo driver 248 drives piezo actuators 252 that actuate the micrometers 96b to adjust the length of the ring-down cavity 84. Each channel has two components: communications to the piezo driver through RS-232, and analog input from the DAQ card 224. In other embodiments, two or more piezo drivers can be employed.

Each optical modulator 60, 68 is driven with an RF driver 256 that sends approximately a 40 MHz signal. Changing the frequency of the RF driver 256 changes the Bragg angle for a given optical wavelength, or changes the optical wavelength that a given or fixed Bragg angle is attuned to. If the RF driver 256 is tuned to a specific frequency and set to full power, most of the working beam 52 (about 85%) gets through. If adjusted to 80%, 70%, then the optical modulator 60, 68 will attenuate. If the RF driver 256 is set to zero, the optical modulator 60, 68 shuts off completely. The frequency of the RF driver is set through a component via RS232. An analog and digital component can set the amplitude and the on/off condition of the RF driver 256. In particular, the DAQ card 224 sends a signal to the timing circuit 260 which, in turn, generates the four necessary signals needed to enable and set the amplitude of the RF drivers. The timing circuit 260 can operate in a steady state condition or a ring-down triggering condition where the timing circuit 260 sets the four voltages to zero, and then returns to the previous voltage level after a pre-determined amount of time.

There is a digital output ("DO") from the DAQ card 224 that controls the timing circuit 260 via a digitizer 264.

The computer 204 is a control system that is coupled to the pressure sensor 128 to receive measured pressure therefrom, and to the gas intake valve 124a controlling fluid communication between the gas source 116 and the thermal desorption tube 104. The computer 204 is conditionable to a sample loading mode, in which it controls the gas intake valve 124a to repeatedly open and close to introduce more of the gas from the gas source 116 until the pressure measured by the pressure sensor 128 is at the target sample pressure.

Referring again to FIG. 1, once the gaseous sample is loaded in the ring-down cavity 84, one laser 24 or 28 is tuned to a specific wavelength and its light is directed through the first optical modulator 60, reflected by the mirror 64, through the second optical modulator 68, focused by the focusing lens 72, and reflected by the mirror 76 to the ring-down chamber 80. The optical modulators 60, 68 attenuate the working beam 52 somewhat to modulate its intensity.

When the working beam 52 reaches the front cavity mirror 88a, a fraction, about 0.1%, penetrates the front cavity mirror 88a to enter the ring-down cavity 84. The majority of the working beam, about 99.9%, is initially reflected back along the same path to the working laser 24 or 28.

Initially, the ring-down cavity 84 is not illuminated. Light enters the ring-down cavity 84 and, as the majority of the light in the ring-down cavity 84 is reflected between the two cavity mirrors 88, the amount, or power, of light in the ring-down cavity 84 starts increasing as further light is introduced from outside via the working beam 52. A certain fraction of the light leaks out past the cavity mirrors 88. It takes a duration of time to "fill" the ring-down cavity 84 with light, and this can occur when the cavity length is equal to an adjacent resonance length of the ring-down cavity 84 for the tuned laser. At that point, there is an equilibrium between the incoming light and the leakage. Once this equilibrium is achieved, the laser 24, 28 is extinguished or otherwise stopped from entering the ring-down cavity 84 via the optical modulators 60, 68. In other embodiments, the laser can be detuned so that it does not resonate for the configured cavity length.

The timing circuit 260 simultaneously directs the first and second optical modulators 60, 68 to attenuate the light beam at or close to an attenuation limits of the optical modulators 60, 68 to reduce an intensity of the light beam from the first optical modulator 60. In the CRDS system 20, by directing both optical modulators 60, 68 to shut off simultaneously, the amount of light deflected by the first optical modulator 60 during the short span of time is markedly reduced by the second optical modulator 68 as it is shutting down.

Extinguishing of the laser light provided to the ring-down cavity 84 enables a ring-down event to be commenced. The resonating laser light provided to the ring-down cavity 84 can be extinguished in other manners in alternative embodiments, such as, for example, by detuning the laser.

During the ring-down event, the computer 204 registers the light intensity data reported by the liquid nitrogen-cooled detector 100 exiting from the back end of the ring-down cavity 84. The ring-down event lasts about ten microseconds in the present configuration, but can last a longer or shorter time in other embodiments. The light decay time is about two microseconds.

About 100 microseconds after when the ring-down event is triggered, the timing circuit 260 directs the optical modulators 60, 68 to recommence allowing the working beam 52 through to the ring-down cavity 84. It is then determined if sufficient ring-down data has been collected. The CRDS system 20 is configured in this embodiment to collect data from 500 ring-down events. If the data from 500 ring-down events has been captured, the computer 204 stops operation of the piezo driver 248, and then determines the decay rate from the ring-down event data. If, instead, it is determined that further ring-down data is to be collected, the computer 204 continues to direct the piezo driver 248 to actuate the rear cavity mirror 88b.

The process is repeated for lights of multiple frequencies to generate an absorption spectrum for the sample. For example, the light generated by the $CO_2$ laser 24 provides absorption coefficients for a range of frequencies. Similarly, absorption coefficients can be generated for a range of frequencies for the light from the carbon-13 $O_2$ laser 28. In this manner, an absorption spectrum can be developed for the sample.

While, in the above-described embodiment, the light sources are two lasers that produce light in the mid-infrared range, it will be appreciated that other light sources can be employed. For example, a laser producing light in the visible spectrum or a near-infrared laser can be employed. Further, in some scenarios, the CRDS system can include only one laser, or three or more lasers, to generate the working beam.

While, in the above-described embodiment, the collection medium is a sorbent tube and, in particular, a thermal desorption tube, other types of collection medium can be employed. For example, solid phase microextraction ("SPME") devices can be employed with the system.

Electro-optic modulators can be used in place of acousto-optic modulators.

The acousto-optic modulators can be configured so that the frequency of the working beam is shifted up or down. As long as the net frequency shift effected by the acousto-optic modulators shifts the frequency of the working beam significantly away from the frequency of the working beam being generated by the laser(s) so that the reflected light is outside of the bandwidth of the laser light being generated, the amount of interference between the reflected light and the generated working beam can be minimized.

In other embodiments, more than two optical modulators can be employed in a CRDS system to provide further extinguishing capacity to more quickly extinguish the working beam at the commencement of a ring-down event. Further, in further embodiments, a single optical modulator can be employed.

One or more focusing lenses can be employed in other embodiments, and translated to enable repositioning of the lenses to allow mode-matching of each wavelength of the lasers.

The same approach can be adopted for other types of resonant cavities, and particularly optical resonant cavities.

Other types of events can be triggered as the cavity length is proximal to the resonance length of the cavity for the particular selected wavelength.

Analysis of the gaseous samples can be performed at pressure levels other than one atmosphere in other embodiments. The breadth of the absorption spectrum may change accordingly.

Although specific advantages have been enumerated above, various embodiments may include some, none, or all of the enumerated advantages.

While, in the above-described embodiment, the resonant cavity is a ring-down cavity, in other embodiments, other types of resonant cavities can be employed.

Persons skilled in the art will appreciate that there are yet more alternative implementations and modifications possible, and that the above examples are only illustrations of one or more implementations. The scope, therefore, is only to be limited by the claims appended hereto.

LIST OF REFERENCE NUMERALS

20 CRDS system
24 $CO_2$ laser
28 carbon-13 $O_2$ laser
32 first laser beam
36 second laser beam
40 mirror
44 beam splitter
48 sampling beam
52 output beam
56 fast infrared detector
60 first optical modulator
64 mirror
68 second optical modulator
72 focusing lens
76 mirror
80 ring-down chamber
84 ring-down cavity
86 inert coating
87 interior surface
88 cavity mirror
88$a$ front cavity mirror
88$b$ rear cavity mirror
92 mirror mounts
96 micrometer
96$a$ mechanized micrometer
96$b$ piezoelectric micrometer
100 liquid nitrogen-cooled detector
104 thermal desorption tube
108 sample-receiving end
110 exhaust end
112 sample loading system
116 nitrogen gas source
120 gas supply conduit
120$a$ gas intake line
120$b$ pathing line
120$c$ tube exhaust line
121 sample supply conduit
121$a$ initial portion
121$b$ secondary portion
122 bypass conduit
123 tube exhaust conduit
124 valve
124$a$ gas intake valve
124$b$ auxiliary gas intake valve
124$c$ bypass conduit valve
124$d$ cavity inlet valve
124$e$ pathing valve
124$f$ fore tube isolation valve
124$g$ rear tube isolation valve
124$h$ sample exhaust valve
124$i$ cavity outlet valve
124$j$ vacuum cutoff valve
124$k$ vacuum intake valve
128 pressure sensor
130$a$, 130$b$ filter
132 heater
136 mass flow controller
140 evacuation conduit
144 pressure sensor
148 vacuum pump
150 pump intake line
152 inert coating
200 electronic control subsystem
204 computer
205 processor
206 storage
208 RF driver
212 grating actuator
216 output coupler piezo
220 high-voltage amplifier
224 DAQ card
228 actuator driver
232 amplifier 236 oscilloscope
240 temperature controller
244 relay board
248 three-channel piezo driver
252 piezo actuator
256 RF driver
260 timing circuit
264 digitizer
300 method of performing spectroscopy
310 couple gas source to sorbent tube
320 couple sorbent tube to resonant cavity
330 flow gas through resonant cavity
340 flow gas through sorbent tube away from resonant cavity
350 heat sorbent tube to target temperature
360 flow gas through sorbent tube to resonant cavity
370 measure pressure via pressure sensor
380 pressure at target sample pressure?
390 perform spectroscopy analysis on loaded sample

What is claimed is:

1. A spectroscopy system, comprising:
a resonant cavity;
a first conduit configured to couple at a first end thereof to a gas source, and at a second end thereof to a first end of a collection medium containing a sample for analysis;
a second conduit configured to couple at a first end thereof to a second end of the collection medium, and at a second end thereof to the resonant cavity; and
a heater positioned to heat the collection medium when the collection medium is coupled to the first conduit and to the second conduit.

2. The spectroscopy system according to claim 1, wherein the collection medium is a sorbent tube.

3. The spectroscopy system according to claim 2, wherein the first end of the sorbent tube is an exhaust end and the second end of the sorbent tube is a sample-receiving end.

4. The spectroscopy system according to claim 3, wherein the gas source provides gas at a source gas pressure above a target sample pressure within the resonant cavity for analysis of the sample.

5. The spectroscopy system according to claim 4, further comprising:
a pressure sensor positioned upstream of the sorbent tube when gas is flowing from the sorbent tube to the resonant cavity.

6. The spectroscopy system according to claim 5, further comprising:
a control system coupled to the pressure sensor to receive measured pressure therefrom, and to a valve controlling fluid communication between the gas source, and the sorbent tube and the pressure sensor, the control system conditionable to a sample loading mode, in which the valve is repeatedly opened and closed to introduce more of the gas from the gas source until the measured pressure is at the target sample pressure.

7. The spectroscopy system according to claim 6, wherein the measured pressure is compared to the target sample pressure when the valve is closed.

8. The spectroscopy system according to claim 7, wherein the valve is a first valve, and wherein the spectroscopy system further comprises:
a second valve positioned along the second conduit;
a third conduit in fluid communication with the first conduit and in fluid communication with the second conduit at a position between the second valve and the sorbent tube;
a third valve controlling fluid communication through the third conduit;
a fourth conduit in fluid communication with the first conduit between the first valve and the sorbent tube; and
a fourth valve positioned along the first conduit between the third conduit and the fourth conduit.

9. The spectroscopy system according to claim 8, wherein the pressure sensor is positioned along the third conduit between the first conduit and the third valve.

10. The spectroscopy system according to claim 9, further comprising:
a fifth valve positioned along the second conduit between the third conduit and the sorbent tube.

11. The spectroscopy system according to claim 10, wherein the spectroscopy system further comprises:
a sixth valve positioned along the first conduit between the sorbent tube and the fourth conduit.

12. The spectroscopy system according to claim 10, wherein the control system is configured to operate in a first mode, wherein the control system opens the first valve, the third valve, and the fifth valve and closes the second valve and the fourth valve to flow gas through the sorbent tube and through the fourth conduit, and in a second mode, wherein the control system opens first valve, the fourth valve, the second valve, and the fifth valve and closes the third valve to flow gas through the sorbent tube and into the resonant cavity.

13. The spectroscopy system according to claim 1, further comprising:
a filter positioned along the second conduit.

14. A method of performing spectroscopy, comprising:
coupling a gas source to a first end of a collection medium containing a sample for analysis;
coupling a second end of the collection medium to a resonant cavity;
heating the sorbent tube to a target temperature; and
flowing gas from the gas source through the collection medium and into the resonant cavity.

15. The method according to claim 14, wherein the collection medium is a sorbent tube.

16. The method according to claim 14, wherein the first end of the sorbent tube is an exhaust end and the second end of the sorbent tube is a sample-receiving end.

17. The method according to 16, further comprising:
measuring the pressure in the resonant cavity via a pressure sensor positioned upstream of the sorbent tube when gas is flowing from the sorbent tube to the resonant cavity.

18. The method according to claim 17, further comprising:
repeatedly opening and closing a valve controlling fluid communication between the gas source and the sorbent tube until the measured pressure matches a target sample pressure level.

19. The method according to claim 18, wherein the measured pressure is compared to the target sample pressure level when the valve is closed.

20. The method according to claim 17, wherein the flowing gas includes flowing gas through the sorbent tube from a first end of the sorbent tube to a second sample-receiving end of the sorbent tube, the method further comprising:
flowing gas through the sorbent tube from the sample-receiving end thereof to the exhaust end thereof.

21. The method according to claim 17, further comprising:
    filtering the flowing gas before the flowing gas enters the resonant cavity.

22. A spectroscopy system, comprising:
    a resonant cavity having a first mirror positioned towards a first end thereof and a second mirror positioned towards a second end thereof and at least one interior surface extending between the first mirror and the second mirror, wherein the at least one interior surface is chemically inert.

23. The spectroscopy system according to claim 22, further comprising:
    a sample-loading system coupled to the resonant cavity and having at least one conduit therein extending between a sample source and the resonant cavity, wherein the conduit has an inert coating on an interior surface thereof.

24. The spectroscopy system according to claim 22, further comprising:
    a sample-loading system coupled to the resonant cavity and having at least one conduit therein extending between the resonant cavity and an exhaust outlet, the at least one conduit having a valve positioned therealong, wherein a portion of the at least one conduit extending between the resonant cavity and the valve has an inert coating on an interior surface thereof.

25. The spectroscopy system according to claim 22, further comprising:
    a filter positioned to filter a gas before the gas enters the resonant cavity.

\* \* \* \* \*